(12) United States Patent
Benna et al.

(10) Patent No.: US 11,607,567 B2
(45) Date of Patent: Mar. 21, 2023

(54) MODULAR MULTI-ROOM PROTON THERAPY SYSTEM

(71) Applicants: Varian Medical Systems Particle Therapy GmbH, Troisdorf (DE); Varian Medical Systems, Inc., Palo Alto, CA (US)

(72) Inventors: Manuel Benna, Bad Honnef (DE); Vladimir Anferov, Bloomington, IN (US); Andrii Rusanov, Troisdorf (DE)

(73) Assignees: Varian Medical Systems, Inc, Palo Alto, CA (US); Varian Medical Systms Particle Therapy GmbH & Co. KG, Torisdorf (DE)

( * ) Notice: Subject to any disclaimer, the term of this patent is extended or adjusted under 35 U.S.C. 154(b) by 906 days.

(21) Appl. No.: 16/425,552

(22) Filed: May 29, 2019

(65) Prior Publication Data
US 2020/0376300 A1    Dec. 3, 2020

(51) Int. Cl.
*A61N 5/10* (2006.01)
*H05H 7/10* (2006.01)
*H05H 7/04* (2006.01)

(52) U.S. Cl.
CPC ......... *A61N 5/1079* (2013.01); *A61N 5/1081* (2013.01); *H05H 7/04* (2013.01); *H05H 7/10* (2013.01); *A61N 2005/1087* (2013.01); *A61N 2005/1092* (2013.01); *H05H 2007/048* (2013.01)

(58) Field of Classification Search
CPC ................ A61N 5/1079; A61N 5/1081; A61N 2005/1087; A61N 2005/1092; H05H 7/04; H05H 7/10; H05H 2007/048
USPC ................................ 600/1; 250/492.1, 492.3
See application file for complete search history.

(56) References Cited

U.S. PATENT DOCUMENTS

2008/0234531 A1*  9/2008  Welch ...................... A61N 5/10
                                                                    600/2

\* cited by examiner

*Primary Examiner* — Nicole M Ippolito

(57) ABSTRACT

Embodiments of the present invention describe systems and methods for providing proton therapy treatment using a beam line where the ESS is reduced or eliminated. For multi-room configurations, a beam line is included having quadrupole and steerer magnets to align and focus a particle beam extracted by an accelerator and guided by a bend section. A degrader is disposed between the bend section and the treatment room, and the energy analyzing functionality is performed by the gantry.

17 Claims, 8 Drawing Sheets

MODULAR MULTI-ROOM PROTON THERAPY SYSTEM

FIELD

Embodiments of the present invention generally relate to the field of proton therapy medical devices. More specifically, embodiments of the present invention relate beam transfer lines for proton therapy systems.

BACKGROUND

Typical proton therapy treatment systems utilize fixed-energy cyclotrons as proton accelerators followed by an energy selection system (ESS). The energy selection system consists of an energy degrader for reducing the beam energy and a beam energy analyzer (or selector) that reduces the energy spread induced by the degrader. The beam energy analyzer typically used in existing proton therapy treatment systems is a separate achromatic beam line consisting of two or more dipoles and a moveable slit system.

Multi-room proton therapy treatment systems have typically relied on a single ESS. However, using a full-scale energy selection systems with energy degrader and separate beam energy analyzer is expensive in terms of cost of goods and requires a relatively large amount of space to accommodate the complex achromatic beam line. What is needed is a reduced-complexity beam line that reduces the cost of goods and reduces the footprint of the proton therapy treatment system for both single-room and multi-room configurations.

With regard to FIG. 1, an exemplary prior art proton therapy system 155 including an ESS 165 with a separate energy analyzer for supporting multiple gantry treatment rooms 185, 190, and 195, and a fixed beam room 197 with a scanning nozzle is depicted. The energy selection system 165 consists of an energy degrader for reducing the beam energy and a beam energy analyzer (or selector) that reduces the energy spread induced by the degrader. The beam energy analyzer is a separate achromatic beam line consisting of two or more dipoles and a moveable slit system. Bend sections 170, 175, and 180 direct the beam line to treatment rooms 185, 190, and 195, respectively.

The ESS of existing prior art proton therapy system require the use of a separate achromatic beam line consisting of two or more dipoles and a moveable slit system for implementing the energy selection system 165, which typically requires several weeks commission time and significant building and installation costs. Moreover, the magnets required to operate the separate achromatic beam line are relatively large and require large power supplies and external water cooling systems.

Furthermore, the prior art proton therapy system 155 disadvantageously requires a relatively long time to switch energy levels for providing different treatments, which impacts the patient/user experience due to long wait times. For example, in some cases it can take 20 seconds or longer before a patient can receive treatment at the adjusted energy level.

Another disadvantage of the prior art proton therapy system 155 is the requirement to use large water cooling lines up to 6" in diameter to cool the magnets using expensive de-ionized water. The large water cooling lines take up a significant space, leading to a much larger installation footprint and much higher costs. Furthermore, the power supply for the magnets also require expensive cooling and draw significant amounts of power.

Therefore, a significant need exists in the field of proton therapy to reduce the complexity of existing proton therapy treatment systems to address the issues described above.

SUMMARY OF THE INVENTION

Embodiments of the present invention describe systems and methods for providing proton therapy treatment using a beam line where the ESS is reduced or eliminated. For multi-room configurations, a beam line is included having quadrupole and steerer magnets to align and focus a particle beam extracted by an accelerator and guided by a bend section. A degrader is disposed between the bend section and the treatment room, and the energy analyzing functionality is performed by the gantry.

According to one embodiment, a proton treatment system is disclosed. The proton treatment system includes an accelerator operable to extract a particle beam, a beam line including quadrupole and steerer magnets operable to align and focus the particle beam, a bend section coupled to the beam line for directing the particle beam to a treatment room, a degrader disposed between the bend section and the treatment room, where the particle beam is focused on the degrader to modulate an energy of the particle beam, and a gantry disposed in the treatment room and operable to receive the particle beam downstream from the degrader, where the gantry provides energy selection functionality for the treatment room.

According to a different embodiment, a modular multi-room proton treatment system is disclosed. The modular multi-room proton treatment system includes an accelerator operable to extract a particle beam for delivery to a plurality of treatment rooms, a beam line operable to receive the particle beam from the accelerator and comprising quadrupoles and steerer magnets operable to transport the particle beam, a degrader disposed between the beam transfer line and a first bend section, where the degrader is operable to reduce an energy of the particle beam for the plurality of treatment rooms, and a first gantry disposed in a first treatment room and coupled to the first bend section, where the first gantry provides energy selection functionality for the first treatment room.

According to another embodiment, a modular multi-room proton treatment system is disclosed. The modular multi-room proton treatment system includes an accelerator operable to extract a particle beam, a beam line comprising quadrupole and steerer magnets operable to align and focus the particle beam from the accelerator to deliver the particle beam to a first treatment room and a second beam line, a first bend section coupled to the second beam line and operable to direct the particle beam to a first treatment room, a degrader disposed between the first bend section and the first treatment room, where the particle beam is focused on the degrader to modulate an energy of the particle beam, and a first gantry disposed in the first treatment room and operable to receive the particle beam downstream from the degrader, where the first gantry provides energy selection functionality for the first treatment room.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
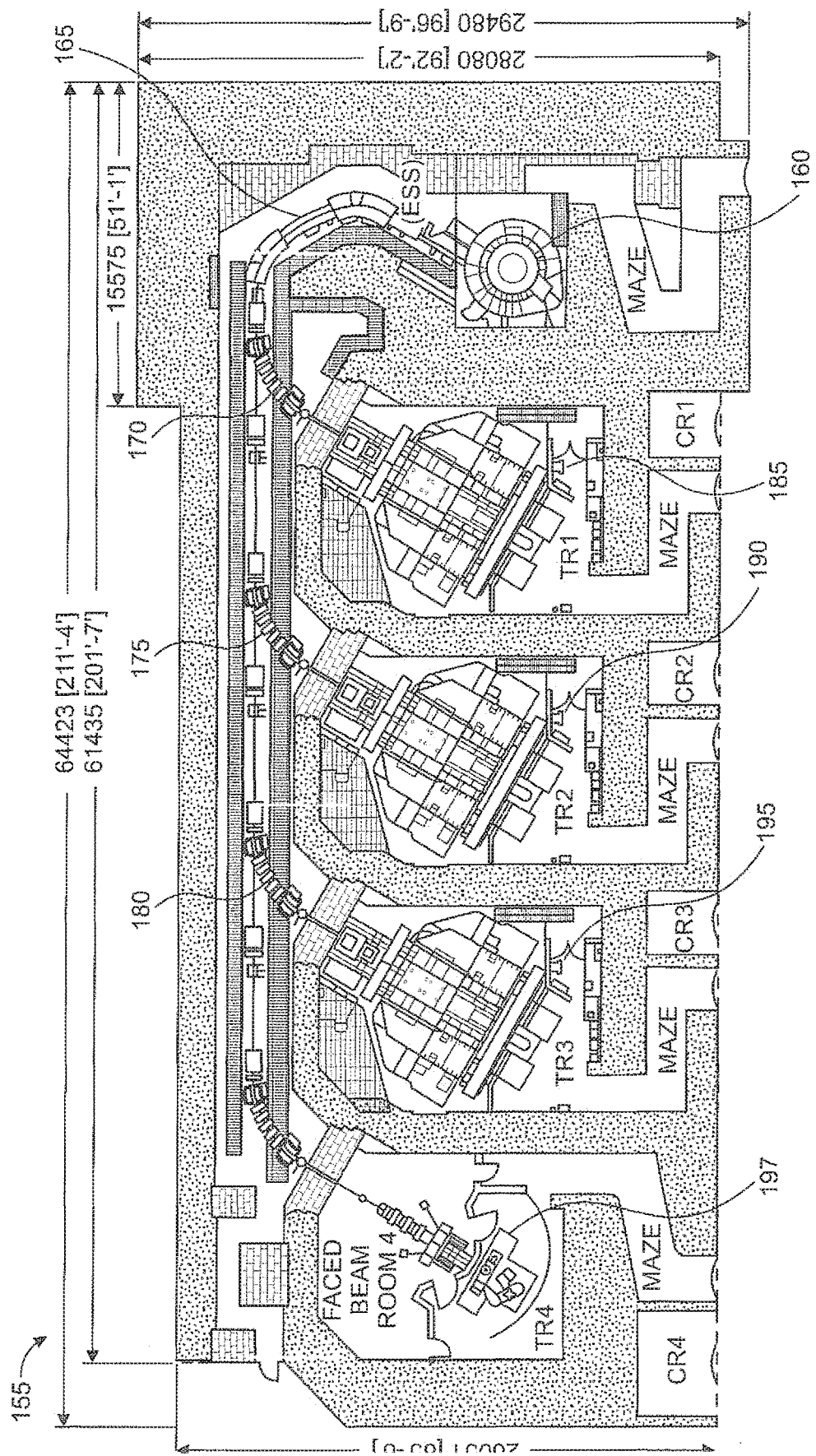
FIG. 1 depicts an exemplary prior art proton therapy system including an ESS with a separate energy analyzer for supporting multiple gantry treatment rooms and a fixed beam room with a scanning nozzle.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "displaying," "writing," "including," "storing," "rendering," "transmitting," "instructing," "associating," "identifying," "capturing," "controlling," "encoding," "decoding," "monitoring," "imaging," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Proton Therapy System with Reduced-Complexity Beam Transfer Line

Embodiments of the present invention describe proton therapy systems that include a reduced-complexity (e.g., simplified) beam transfer line (beam line) such that a large portion of the ESS is reduced or eliminated, and a dedicated degrader is positioned directly in front of the treatment rooms. The embodiments described herein can be used in both single-room and multi-room configurations. For multi-room configurations, a simple fixed-energy beam line distributes the proton beam to separate degraders for each treatment room. In other embodiments, only one degrader per system is used, positioned between the cyclotron and the first bend section. The energy analyzing ability can be performed by either the bend section itself or the gantry beam line.

Due to the simplified nature of the beam transfer line used by embodiments of the present invention, the commission and installation time is much shorter compared to existing systems that require a separate achromatic beam line consisting of two or more dipoles and a moveable slit system for implementing an energy selection system, which typically require several weeks commission time. The reduced complicity beam transfer line also significantly reduces building and installation costs of the proton therapy system. Moreover, embodiments of the present invention do not require large magnets used to operate the separate achromatic beam line in existing systems, which require heavy duty machinery (e.g., heavy lifters) to install at the installation site. In contrast, embodiments of the present invention use relatively light weight magnets that can be installed manually without heavy machinery. Furthermore, the magnets advantageously do not require as much cooling and power compared the magnets of existing systems, and therefore the requirement to use large water cooling pipes to cool the magnets is eliminated. Instead, embodiments of the present invention can utilize air cooling to cool the magnets, which significantly reduces the cost of the proton therapy system. As an additional benefit, the smaller magnets utilized by embodiments of the present invention significantly reduce the radiation shielding requirements thereof, which further reduces the cost of goods and the footprint of the overall proton therapy system.

The multi-room configuration design is modular and consists of any N-number of rooms. The multi-room configuration can be later upgraded to any number of rooms after the initial installation of the treatment system. The treatment room type can be a gantry room or a fixed beam room. Each room type can be either equipped with a scanning nozzle or a scattering nozzle, for example, and each nozzle type can be upgraded to use apertures or moving collimators. A simple beam exit can also be used for each room type.

The reduced-complexity beam transfer lines described herein include one or more energy degraders. The energy analyzing functionally is implemented either in the bend section into room beam line or in the gantry beam line. The gantry beam line offers limited energy acceptance itself, and therefore movable energy slit systems used in typical multi-room configurations are not required.

The reduced-complexity beam transfer lines described herein according to embodiments of the present invention allow for the footprint of the overall proton therapy system to be significantly reduced. Furthermore, the cost of goods for the proton therapy system is reduced because fewer components are required for the beam transfer line. For example, according to some embodiments, the proton therapy system does not require the gantry or gantries thereof to include an energy slit, collimator, or aperture.

The beam lines described herein are shorter in length compared to traditional beam lines and can use fewer quadrupoles for beam transportation. The quadrupoles can be warm magnets or permanent magnets, for example. The number of quadrupoles is reduced compared to traditional systems because the monoenergetic beam produced by the accelerator is fairly well-focused. Moreover, the bend sections describe herein use relatively small magnets to direct the particle beam treatment rooms without requiring additional quadrupoles for chromaticity compensation.

Embodiments of the present invention employ fewer magnets compared to traditional beam lines which allows the proton therapy systems described herein to switch more rapidly between treatment rooms compared to existing proton therapy systems. While typical proton therapy systems using beam transport lines with traditional energy selection systems require approximately 20-30 seconds, for instance, to begin operating in a different treatment room, including time for de-energizing magnets, time for re-energizing magnets, and time for configuring an energy degrader for a specific energy, embodiments of the present invention advantageously provide energy to different treatment rooms with only a few seconds of downtime in-between. The limited downtime between providing energy to different treatment rooms makes the treatment systems of the present invention more efficient compared to traditional systems, thereby significantly improving the patient/user experience due to much shorter wait times between treatments.

Figure 2A:
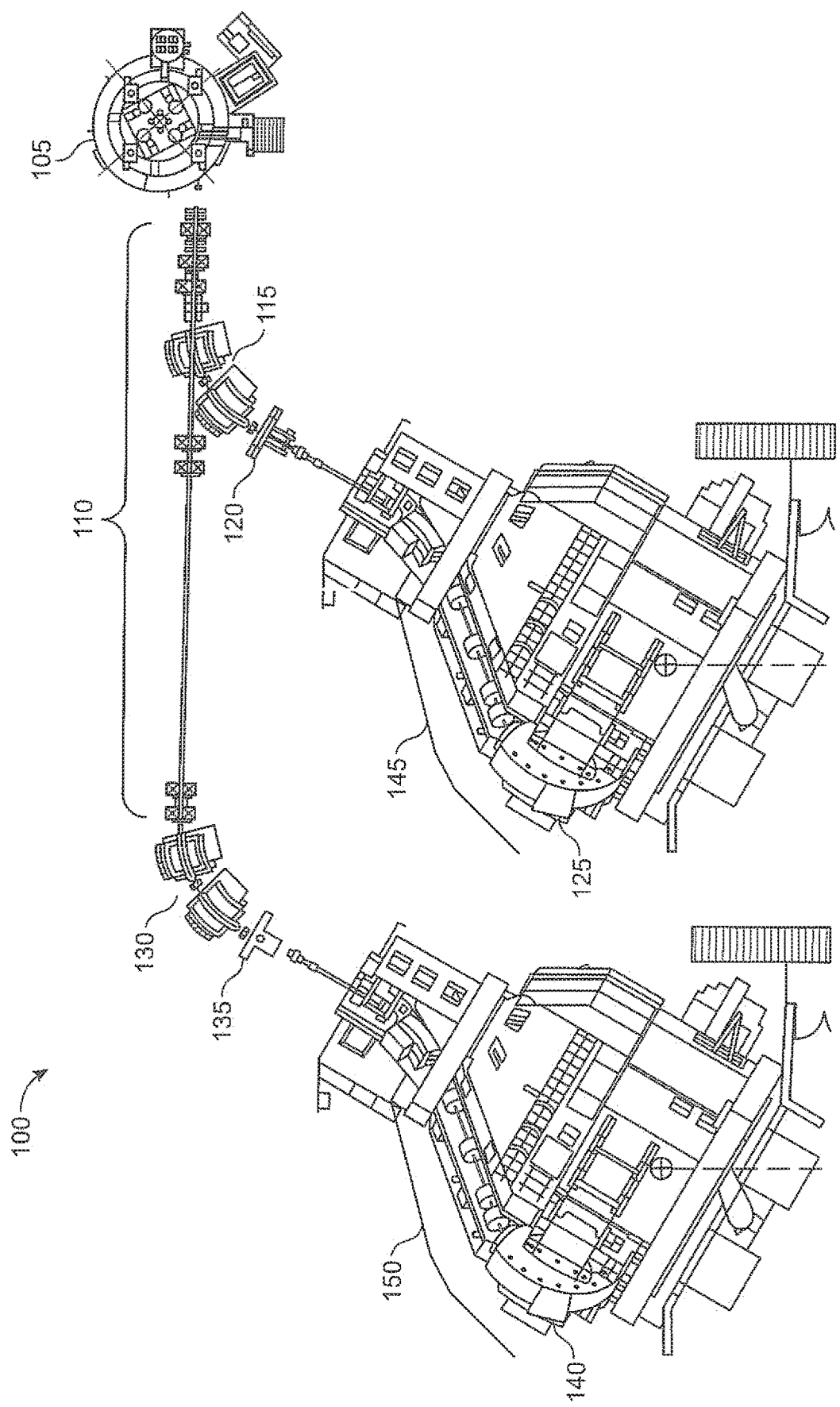
FIG. 2A depicts an exemplary modular multi-room proton treatment system including two gantries configured to provide energy selection functionality according to embodiments of the present invention.

With regard to FIG. 2A, an exemplary multi-room proton therapy system 100 including a reduced-complexity, monoenergetic beam transfer line 110 is depicted according to embodiments of the present invention. An accelerator (e.g., a cyclotron) 105 extracts a particle beam with monoenergetic energy. A monoenergetic beam transfer line 110 transports the beam into one or more treatment rooms. The proton therapy system 100 does not include an energy analyzer component requiring a separate achromatic beam line (e.g., consisting of two or more dipoles and a moveable slit system) because the ESS functionality is performed by the gantries 125 and 140, which advantageously reduces the complexity of the proton therapy system 100.

As depicted in FIG. 1, the monoenergetic beam transfer line 110 transports the beam to gantries 125 and 140, where the gantries 125 and 140 are installed in treatment rooms 145 and 150, respectively. One of ordinary skill in the art will recognize that any conventional particle accelerator used in proton therapy systems can be used to extract a particle beam within the scope of the various embodiments described herein.

The beam transfer line 110 depicted in FIG. 2A uses a monoenergetic beam transfer line layout. Therefore, the bend sections for directing the beam into a treatment room do not require additional quadrupoles to match the achromaticity of the beam. By using a monoenergetic beam transfer line, the number of magnets required to transport the beam is significantly reduced. Moreover, the magnets can be permanent magnets that require no power consumption, or normal magnets can be used that are powered by relatively inexpensive power supplies because the magnets do not need to be ramped. Furthermore, the magnets do not require the large and expensive water cooling system of traditional systems, further reducing the complexity and cost of the proton therapy system 100.

Bend sections 115 and 130 are used to direct the energy beam to treatment rooms 145 and 150. Degraders 120 and 135 are positioned directly in front of treatment rooms 145 and 150 such that the energy spread is limited on the gantry without requiring additional beam line elements. Degraders 120 and 135 provide energy modulation for the beam necessary to provide efficient patient treatment.

Gantries 125 and 140 are used to direct the proton beam to a target region of the patient for providing proton therapy and include ESS functionality rather than requiring separate components for providing ESS functionality, such as energy degraders for reducing the beam energy and separate beam energy analyzers for reducing the energy spread induced by degraders. According to some embodiments, gantries 125 and 140 do not include collimators, slits, or apertures for modifying the beam energy.

Figure 2B:
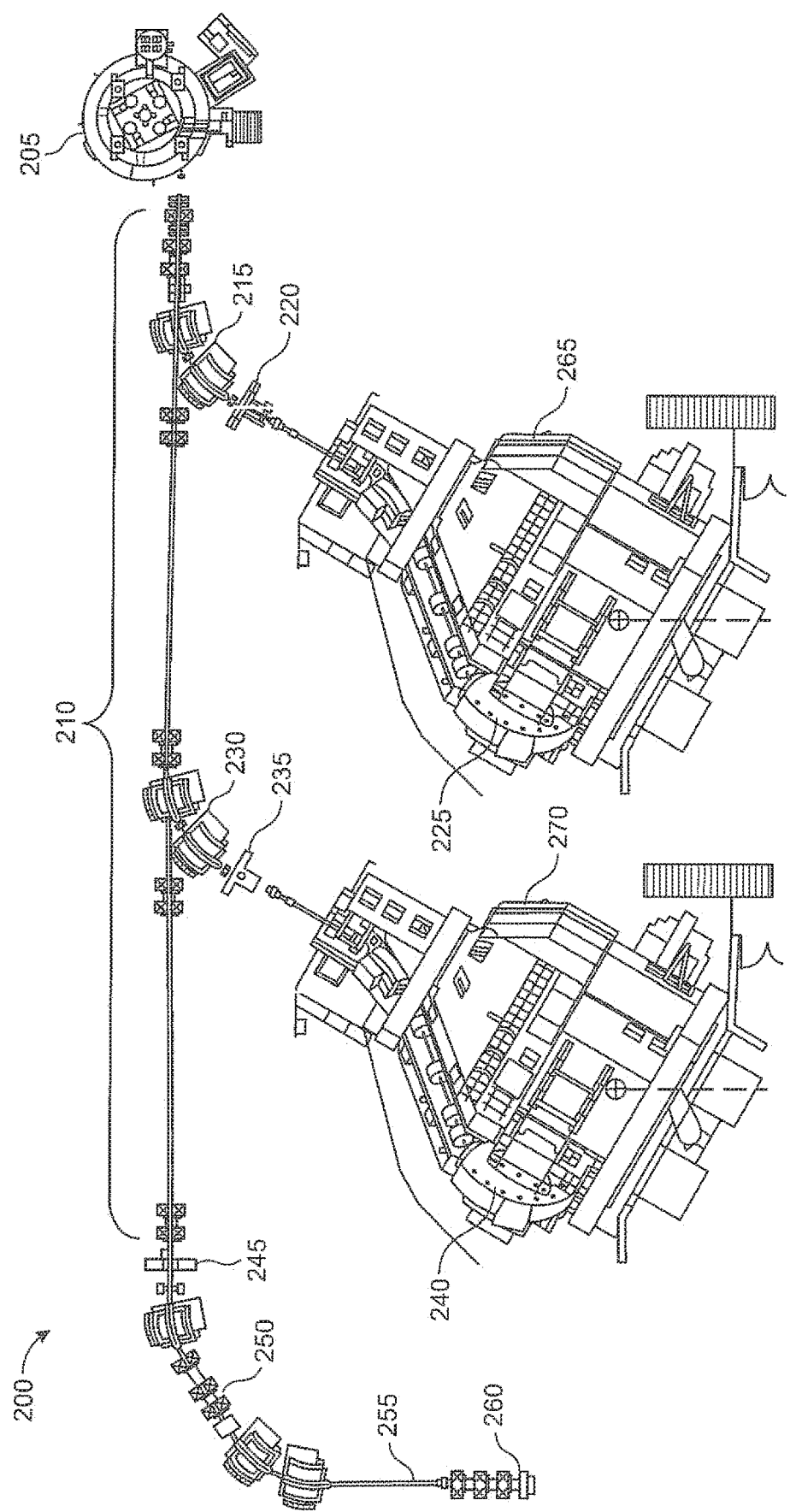
FIG. 2B depicts an exemplary modular multi-room proton treatment system including three treatment rooms and two gantries configured to provide energy selection functionality according to embodiments of the present invention.

With regard to FIG. 2B, an exemplary multi-treatment room proton therapy system 200 including a reduced-complexity, monoenergetic beam transfer line 210 coupled to a fixed beam line is depicted according to embodiments of the present invention. An accelerator (e.g., a cyclotron) 205 extracts a particle beam with monoenergetic energy. Monoenergetic beam transfer line 210 transports the beam into one or more treatment rooms. As depicted in FIG. 2B, the monoenergetic beam transfer line 210 transports the beam to gantries 225 and 240, where the gantries 225 and 240 are installed in separate treatment rooms 265 and 270, respectively, and to fixed beam line 255 coupled to a scattering nozzle or scanning nozzle 260 (e.g., an eye nozzle).

The beam transfer line 210 depicted in FIG. 2B uses a monoenergetic beam transfer line layout. Therefore, the bend sections for directing the beam into a treatment room do not require additional quadrupoles to match the achromaticity of the beam. By using a monoenergetic beam transfer line, the number of magnets required to transport the beam is significantly reduced. In addition, the magnets used can be permanent magnets that require no power consumption, or normal magnets can be used that are powered by relatively inexpensive power supplies because the magnets do not need to be ramped. Furthermore, the magnets do not require the large and expensive water cooling system of traditional systems, further reducing the complexity and cost of the proton therapy system 200.

Bend sections 215 and 230 direct the energy beam produced by the accelerator 205 into treatment rooms 265 and 270. Degraders 220 and 235 are positioned directly in front of treatment rooms 265 and 270 such that the energy spread is limited on the gantry without requiring additional beam line elements. Degraders 220 and 235 provide energy modulation for the beam necessary to provide efficient patient treatment.

An additional bend section 250 directs the beam to fixed beam line 255 and is preceded by a degrader 245 for performing energy modulation by focusing the energy beam on the degraders. The bend 250 includes an energy slit for providing energy analyzing functionality. In contrast, the energy analyzing functionality for rooms 260 and 265 is advantageously performed by gantries 225 and 240 without requiring separate ESS components. The proton therapy system 200 does not include an energy analyzer component requiring a separate achromatic beam line (e.g., consisting of two or more dipoles and a moveable slit system) because the ESS functionality is performed by the gantries 255 and 240, which advantageously reduces the complexity of the proton therapy system 200.

Figure 3:
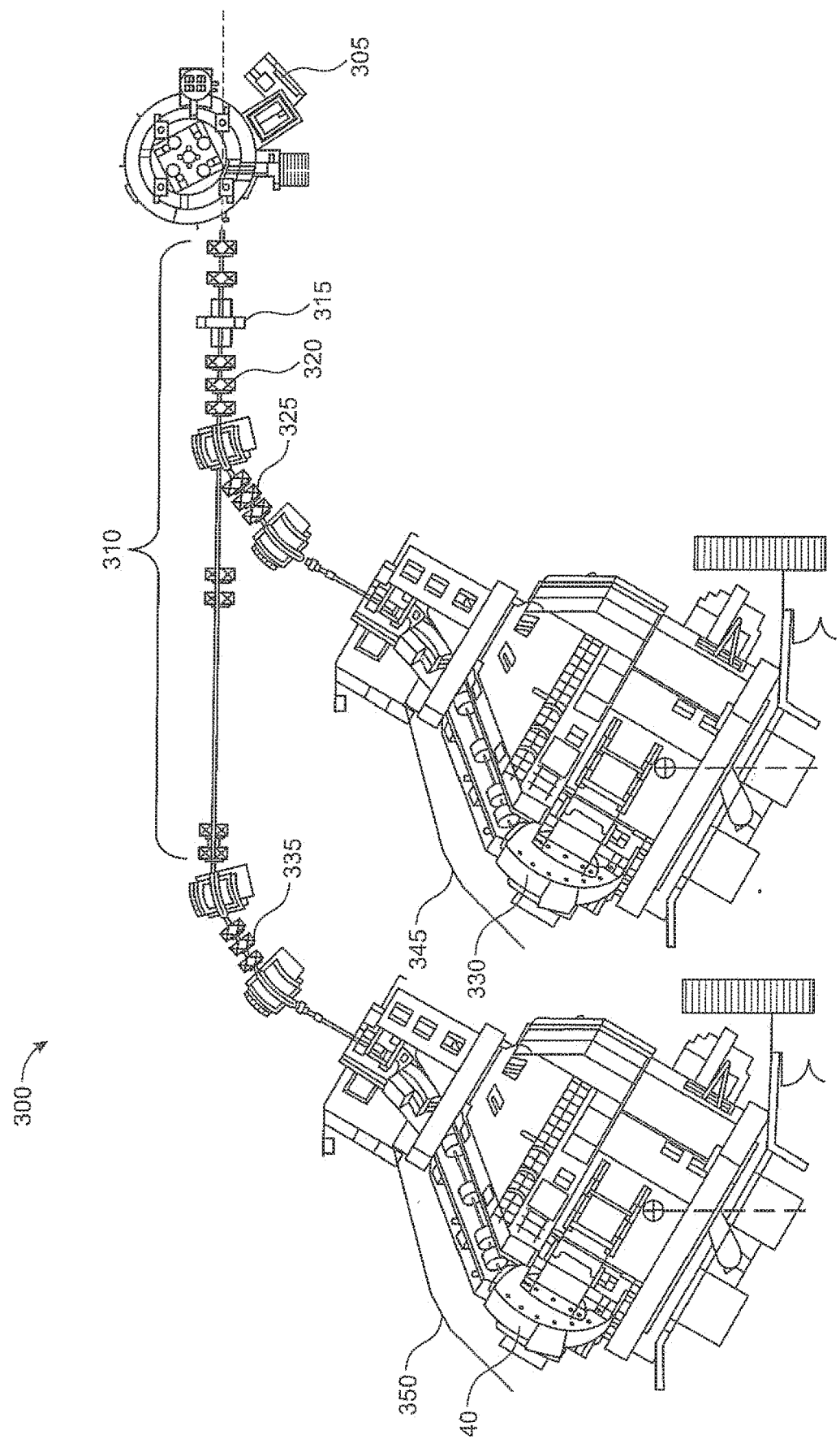
FIG. 3 depicts an exemplary modular multi-room proton treatment system including gantries configured to provide energy selection functionality and a single degrader according to embodiments of the present invention.

With regard to FIG. 3, an exemplary multi-room proton therapy system 300 including a reduced-complexity beam transfer line 310 with a single degrader 315 is depicted according to embodiments of the present invention. An accelerator (e.g., a cyclotron) 305 extracts a particle beam and beam transfer line 310 transports the beam into one or more treatment rooms. In this embodiment, the energy degrading portion of the energy selection system 320 is positioned just before the first bend 325. Beam transfer line 310 transports the beam to gantries 330 and 340, where the gantries 330 and 340 are installed in separate treatment rooms 345 and 350, respectively.

In this case, beam transfer line 310 is not monoenergetic and requires additional quadrupoles installed in bends 325 and 335 to perform chromatic matching of the beam. According to some embodiments, the quadrupoles installed in the bends 325 and 335 include electrical magnets that can be cooled by air and are operable to be powered by a power supply. By combining the traditional ESS 320 with the first bend section 325, the overall footprint of the proton therapy system 300 is advantageously reduced compared to traditional proton therapy systems that utilize an achromatic beam line with multiple dipoles. The energy analyzing portion for the proton therapy system 300 is performed either in the gantry beam line with limited energy acceptance of the gantries 330 and 340, or in-between the bends sections 325 and 335.

Figure 4:
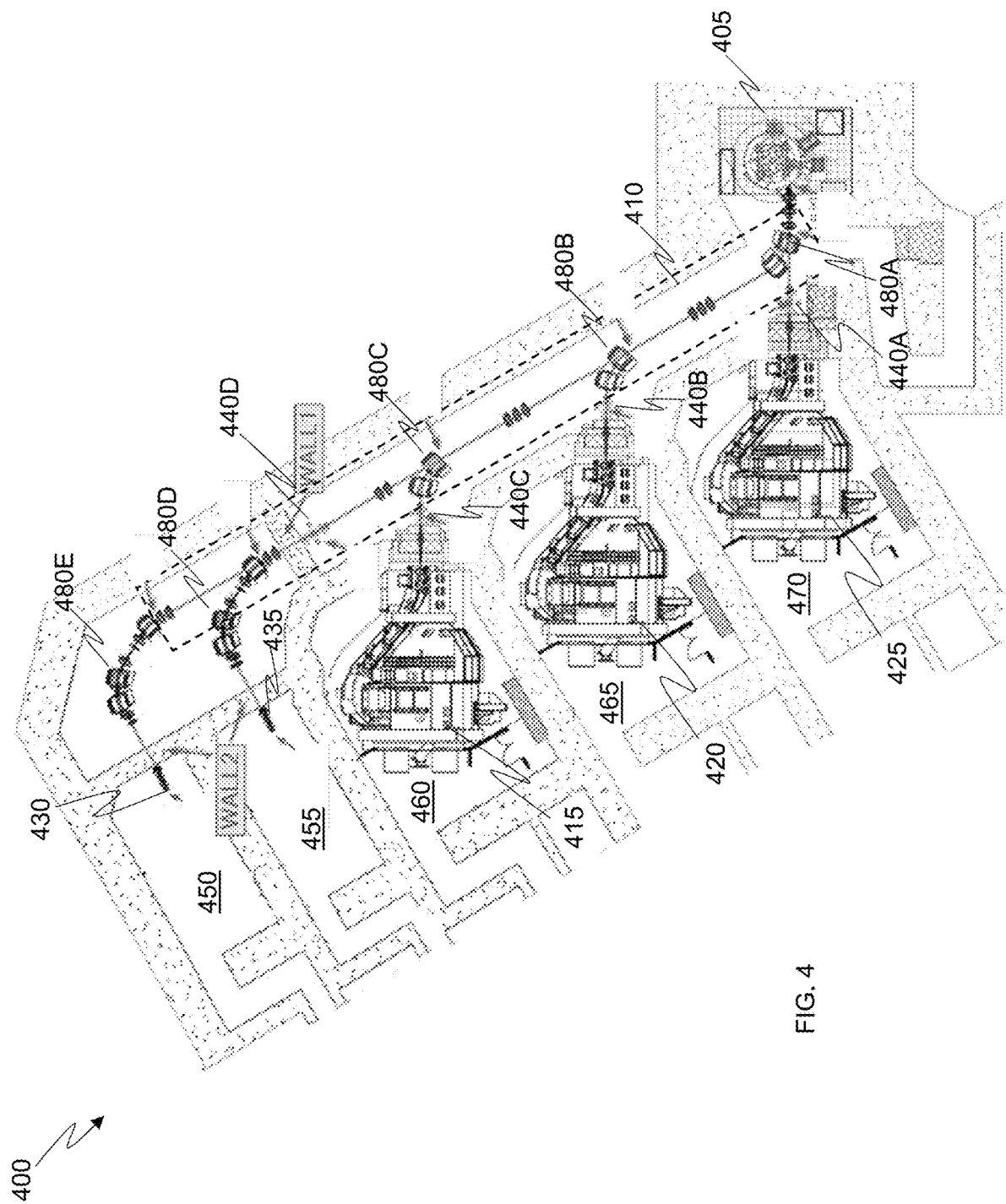
FIG. 4 depicts an exemplary modular multi-room proton treatment system including a beam line having quadrupoles and steerer magnets coupled to three gantry rooms and two fixed beam line rooms according to embodiments of the present invention.

With regard to FIG. 4, an exemplary multi-room proton therapy system 400 including a reduced-complexity, monoenergetic beam transfer line 410 coupled to three gantry rooms 460, 465, and 470, and coupled to two fixed beam line rooms 450 and 455, is depicted according to embodiments of the present invention. An accelerator (e.g., a cyclotron) 405 extracts a particle beam with monoenergetic energy. A monoenergetic beam transfer line 410 transports the beam into treatment rooms 460, 465, and 470. As depicted in FIG. 4, the monoenergetic beam transfer line 410 transports the beam to gantries 415, 420, and 425, installed in separate treatment rooms 460, 465, and 470, and to eye nozzles or scanning nozzles 430 and 435 installed in fixed beam rooms 450 and 455.

The beam transfer line 410 depicted in FIG. 4 uses a monoenergetic beam transfer line layout. Therefore, the bend sections for directing the beam into a treatment room do not require additional quadrupoles to match the achromaticity of the beam. By using a monoenergetic beam transfer line, the number of magnets required to transport the beam is significantly reduced. In addition, the magnets used can be permanent magnets that require no power consumption, or normal magnets powered by relatively inexpensive power supplies because the magnets do not need to be ramped. The magnets are smaller and easier to install, and can be cooled by air without requiring the use of large and expensive water cooling lines.

The energy beam produced by accelerator 405 is fed directly to the first gantry room 470 using a first portion of monoenergetic beam line 410, and a bend section 480A directs the energy beam along the length of a second portion of monoenergetic beam line 410. Bend sections 480B and 480C direct the beam into gantry rooms 460 and 465 for performing proton therapy using gantries 415 and 420. Degraders 440A, 440B, and 440C are positioned directly in front of treatment rooms 460, 465, and 470 such that the energy spread is limited on the gantry without requiring additional beam line elements. Degraders 440A, 440B, and 440C provide energy modulation for the beam necessary to provide efficient patient treatment.

Bend sections 480D and 480E direct the beam to fixed beam line rooms 450 and 455 and are preceded by a degrader 440D for performing energy modulation by focusing the energy beam on the degraders. Fixed nozzles 430 and 435 are coupled to bend sections 480D and 480E for performing beam scanning or scattering. The fixed nozzles 430 and 435 may also be a simple exit window, according to some embodiments. The bend sections 480D and 480E include an energy slit for providing energy analyzing functionality. In contrast, the energy analyzing functionality for rooms 460, 465 and 470 is performed by gantries 415, 420, and 425 without requiring separate ESS components.

As depicted in FIG. 4, shielded walls wall1 and wall2 provide important radiation shielding between rooms. Simplified monoenergetic beam line 410 includes fewer magnets compared to traditional beam lines, and therefore the shielding requirements thereof are reduced compared to traditional proton therapy systems. The reduced-complexity beam line 410 combined with the reduced shielding requirements of the walls significantly reduces the footprint of the treatment system 400 as well as the overall cost of equipment.

Figure 5:
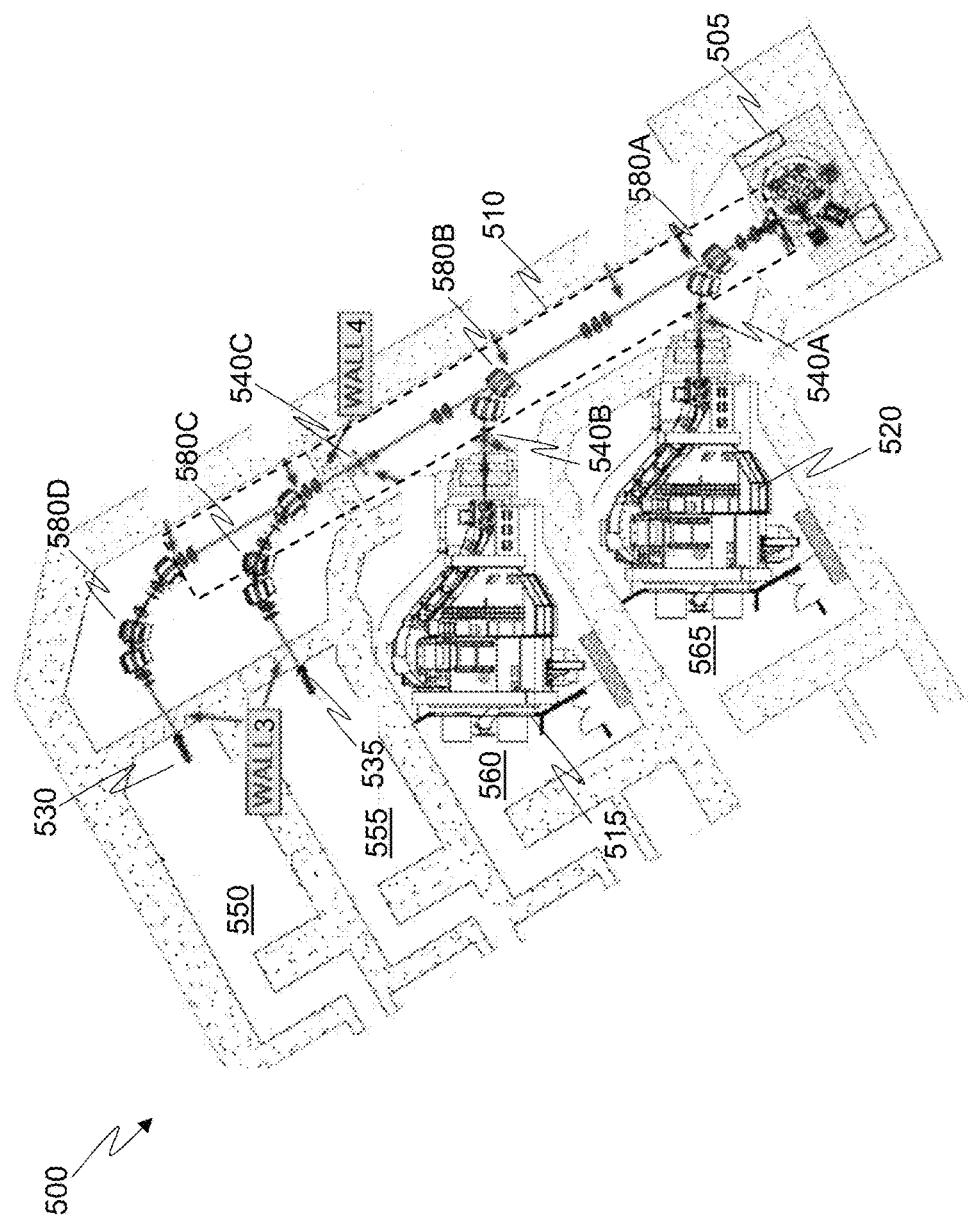
FIG. 5 depicts an exemplary modular multi-room proton treatment system including a beam line having quadrupoles and steerer magnets coupled to two gantry rooms and two fixed beam line rooms according to embodiments of the present invention.

With regard to FIG. 5, an exemplary multi-room proton therapy system 500 including a reduced-complexity, monoenergetic beam transfer line 510 coupled to two gantry rooms 560 and 565, and coupled to two fixed beam line rooms 550 and 555, is depicted according to embodiments of the present invention. An accelerator (e.g., a cyclotron) 505 extracts a particle beam with monoenergetic energy. A monoenergetic beam transfer line 510 transports the beam to the various treatment rooms. As depicted in FIG. 5, the monoenergetic beam transfer line 510 transports the beam to gantries 515 and 520, installed in separate treatment rooms 560 and 565, and to scanning nozzles or scattering nozzles 530 and 535 (e.g., an eye nozzle) installed in fixed beam rooms 550 and 555. The scanning nozzles or scattering nozzles 530 and 535 may also be a simple exit window, according to some embodiments.

The beam transfer line 510 depicted in FIG. 5 uses a monoenergetic beam transfer line layout. Therefore, the bend sections for directing the beam into a treatment room do not require additional quadrupoles to match the achromaticity of the beam. By using a monoenergetic beam transfer line, the number of magnets required to transport the beam is significantly reduced. In addition, the magnets used can be permanent magnets that require no power consumption, or normal magnets powered by relatively inexpensive power supplies because the magnets do not need to be ramped.

A first bend section 580A directs the energy beam produced by accelerator 505 to the first gantry room 565 using monoenergetic beam line 510, and a second bend section 580B directs the energy beam into the second gantry room 560 for performing proton therapy using gantry 515. Degraders 540A and 540B are positioned directly in front of treatment rooms 560 and 565 such that the energy spread is limited on the gantry without requiring additional beam line elements, and provide energy modulation for the beam necessary to provide efficient patient treatment.

Bend sections 580C and 580D direct the energy beam produced by accelerator 505 to fixed beam line rooms 550 and 555 and are preceded by a degrader 540C for performing energy modulation by focusing the energy beam on the degraders. Fixed nozzles 530 and 535 are coupled to bend sections 580C and 580D for performing beam scanning or scattering. The bend sections 580C and 580D include an energy slit for providing energy analyzing functionality. In contrast, the energy analyzing functionality for rooms 560 and 565 is performed by gantries 515 and 520 without requiring separate ESS components.

As depicted in FIG. 5, shielded walls wall3 and wall4 provide critical radiation shielding between rooms. Simplified monoenergetic beam line 510 includes fewer magnets compared to traditional beam lines, and therefore the shielding requirements thereof are reduced compared to traditional proton therapy systems. The reduced-complexity beam line 510 combined with the reduced shielding requirements of the walls significantly reduces the footprint of the treatment system 500 as well as the overall cost of equipment.

Figure 6:
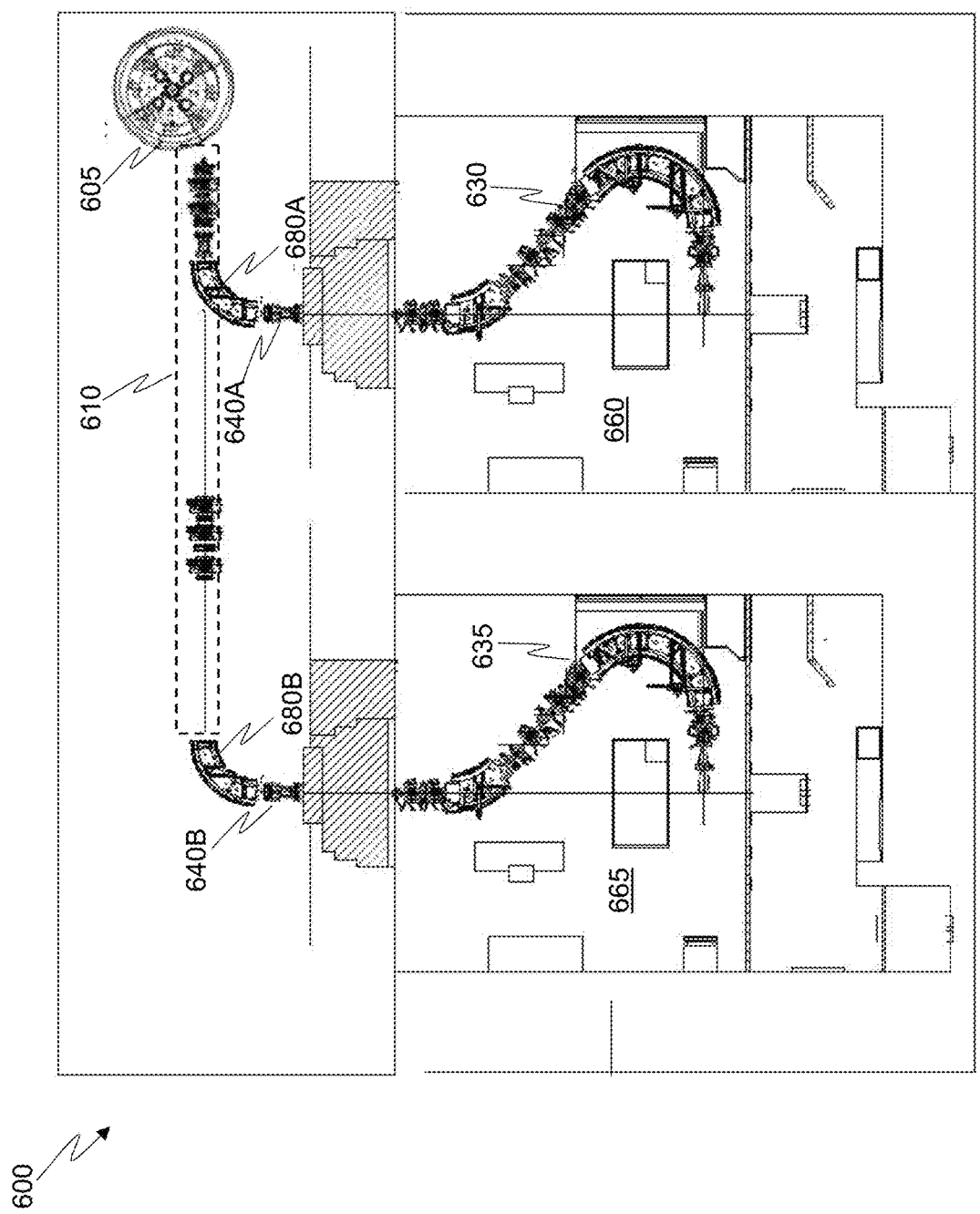
FIG. 6 depicts an exemplary modular multi-room proton treatment system including a beam line having quadrupoles and steerer magnets coupled to two fixed beam line rooms according to embodiments of the present invention.

With regard to FIG. 6, an exemplary proton therapy system 600 including a reduced-complexity, monoenergetic beam transfer line 610 coupled to two fixed beam line rooms 660 and 665 is depicted according to embodiments of the present invention. An accelerator (e.g., a cyclotron) 605 extracts a particle beam with monoenergetic energy. A monoenergetic beam transfer line 610 transports the beam to the various treatment rooms. As depicted in FIG. 6, the monoenergetic beam transfer line 610 transports the beam to scanning or scattering nozzles (e.g., an eye nozzle) 630 and 635 installed in separate treatment rooms 660 and 665, respectively. The scanning nozzles or scattering nozzles 630 and 635 may also be a simple exit window, according to some embodiments.

Bend sections 680A and 680B direct the energy beam produced by accelerator 605 to fixed beam line rooms 650 and 655. Both rooms 650 and 655 are preceded by degraders 640A and 640B for performing energy modulation by focusing the energy beam on the degraders. Fixed nozzles 630 and 635 are coupled to bend sections 680A and 680B for performing beam scanning or scattering. The bend sections 680A and 680B include an energy slit for providing energy analyzing functionality.

Figure 7:
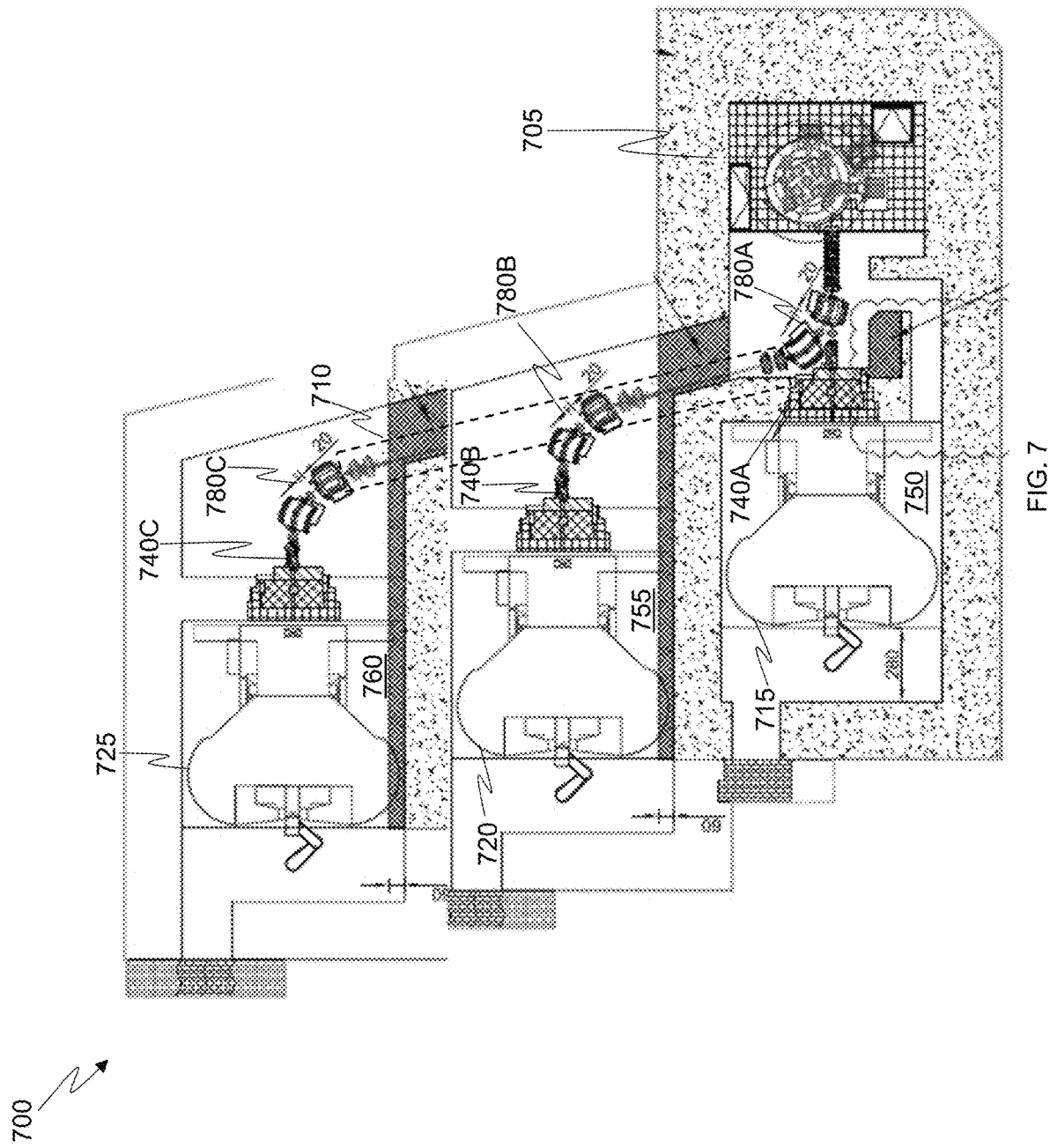
FIG. 7 depicts an exemplary modular multi-room proton treatment including three treatment room with gantries configured to provide energy selection functionality according to embodiments of the present invention.

With regard to FIG. 7, an exemplary stacked proton therapy system 700 including a reduced-complexity, monoenergetic beam transfer line 710 coupled to three gantry rooms 750, 755, and 760 is depicted according to embodiments of the present invention. The compact installation of the proton therapy system 700 is made possible by eliminating the need for an ESS requiring a separate achromatic beam line consisting of two or more dipoles and a moveable slit system for implementing the ESS. Rooms 750, 755, and 760 are positioned in a vertical orientation such that room 755 is located above room 755 and room 760 is located above room 755. An accelerator (e.g., a cyclotron) 705 extracts a particle beam with monoenergetic energy. A monoenergetic beam transfer line 710 transports the beam into treatment rooms 750, 755, and 760. As depicted in FIG. 7, the monoenergetic beam transfer line 710 transports the beam to gantries 715, 720, 725, installed in separate treatment rooms 750, 755, and 760.

The beam transfer line 710 depicted in FIG. 7 uses a monoenergetic beam transfer line layout. Therefore, the bend sections for directing the beam into a treatment room do not require additional quadrupoles to match the achromaticity of the beam. By using a monoenergetic beam transfer line, the number of magnets required to transport the beam is significantly reduced. In addition, the magnets used can be permanent magnets that require no power consumption, or normal magnets can be used that are powered by relatively inexpensive power supplies because the magnets do not need to be ramped.

The energy beam produced by accelerator 705 is fed directly to the first gantry 715 in treatment room 750 using a first portion of monoenergetic beam line 710, and a bend section 780A directs the energy beam along the length of a second portion of monoenergetic beam line 710. Bend sections 780B and 780C direct the energy beam into gantry rooms 755 and 760 for performing proton therapy using gantries 720 and 725, respectively. Degraders 740A, 740B, and 740C are positioned directly in front of treatment rooms 750, 755, and 760 such that the energy spread is limited on the gantry without requiring additional beam line elements. Degraders 740A, 740B, and 740C provide energy modulation for the beam necessary to provide efficient patient treatment. The energy analyzing functionality for rooms 715, 720, and 725 is performed by gantries 715, 720, and 725 without requiring separate ESS components.

According to one embodiment, a proton treatment system is disclosed. The proton treatment system includes an accelerator operable to extract a particle beam, a beam line including quadrupole and steerer magnets operable to align and focus the particle beam, a bend section coupled to the beam line for directing the particle beam to a treatment room, a degrader disposed between the bend section and the treatment room, where the particle beam is focused on the degrader to modulate an energy of the particle beam, and a gantry disposed in the treatment room and operable to receive the particle beam downstream from the degrader, where the gantry provides energy selection functionality for the treatment room.

According to a different embodiment, a modular multi-room proton treatment system is disclosed. The modular multi-room proton treatment system includes an accelerator operable to extract a particle beam for delivery to a plurality of treatment rooms, a beam line operable to receive the particle beam from the accelerator and comprising quadrupoles and steerer magnets operable to transport the particle beam, a degrader disposed between the beam transfer line and a first bend section, where the degrader is operable to reduce an energy of the particle beam for the plurality of treatment rooms, and a first gantry disposed in a first treatment room and coupled to the first bend section, where the first gantry provides energy selection functionality for the first treatment room.

According to another embodiment, a modular multi-room proton treatment system is disclosed. The modular multi-room proton treatment system includes an accelerator operable to extract a particle beam, a beam line comprising quadrupole and steerer magnets operable to align and focus the particle beam from the accelerator to deliver the particle beam to a first treatment room and a second beam line, a first bend section coupled to the second beam line and operable to direct the particle beam to a first treatment room, a degrader disposed between the first bend section and the first treatment room, where the particle beam is focused on the degrader to modulate an energy of the particle beam, and a first gantry disposed in the first treatment room and operable to receive the particle beam downstream from the degrader, where the first gantry provides energy selection functionality for the first treatment room.

According to some embodiments, the beam line transports the particle beam to N number of treatment rooms.

According to some embodiments, the proton treatment system includes N number of bend sections in the beam line operable to bend the particle beam from the degrader into the N number of treatment rooms.

According to some embodiments, the N number of bend sections are operable to perform energy analyzing functionality by modifying an energy width of the proton beam for a fixed beam line room without using a separate achromatic beam line.

According to some embodiments, the proton treatment system includes at least one of: a scanning nozzle; a scattering nozzle; and a simple exit window.

According to some embodiments, the proton treatment system includes a plurality of gantry beam lines operable to provide energy selection functionally for the N number of treatment rooms.

According to some embodiments, the quadrupoles include electrical magnets cooled by air and powered by a power supply.

Embodiments of the present invention are thus described. While the present invention has been described in particular embodiments, it should be appreciated that the present invention should not be construed as limited by such embodiments, but rather construed according to the following claims.

What is claimed is:

1. A modular multi-room treatment system comprising:
   an accelerator operable to extract a particle beam;
   a beam transfer line comprising quadrupole and steerer magnets operable to align and focus said particle beam from said accelerator;
   N number of bend sections coupled to said beam transfer line operable to direct said particle beam to N number of treatment rooms;
   N number of degraders disposed between said N number of bend sections and said N number of treatment rooms, wherein said particle beam is focused on said N number of degraders to modulate an energy of said particle beam; and
   N number of gantries disposed in said N number of treatment room and operable to receive said particle beam downstream from said N number of degraders, wherein said N number of gantries provide energy selection functionality for said N number of treatment rooms.

2. The modular multi-room treatment system described in claim 1, wherein said particle beam comprises a monoenergetic proton beam transported from said accelerator to said degrader.

3. The modular multi-room treatment system described in claim 1, further comprising:
   said N number of bend sections comprising an energy slit for performing energy analyzing functionality;
   an additional degrader disposed on said beam transfer line before said N number of bend sections; and
   a fixed beam transfer line coupled to said N number of bend sections.

4. The modular multi-room treatment system described in claim 1, further comprising a power supply, wherein said bend section comprises electrical dipole magnets powered by said power supply.

5. The modular multi-room treatment system described in claim 1, wherein said bend section comprises permanent dipole magnets.

6. The modular multi-room treatment system described in claim 1, wherein said quadrupoles comprise permanent magnets.

7. The modular multi-room treatment system described in claim 1, wherein said quadrupoles comprise electrical magnets cooled by air and powered by a power supply.

8. The modular multi-room treatment system described in claim 1, wherein said N number of bend section comprise hybrid dipole magnets.

9. A treatment system comprising:
   an accelerator operable to extract a particle beam for delivery to a plurality of treatment rooms;
   a beam line operable to receive said particle beam from said accelerator and comprising quadrupoles and steerer magnets operable to transport said particle beam;
   a first bend section on said beam line for directing said particle beam to said plurality of treatment rooms, wherein said first bend section is operable to perform energy analyzing functionality by modifying an energy width of said particle beam for said first treatment room without using a separate achromatic beam line;
   a degrader disposed between said beam line and said first bend section, wherein said degrader is operable to reduce an energy of said particle beam for said plurality of treatment rooms; and
   a first gantry disposed in a first treatment room and coupled to said first bend section, wherein said first gantry provides energy selection functionality for said first treatment room.

10. The treatment system described in claim 9, wherein said beam line transports said particle beam to N number of treatment rooms.

11. The treatment system described in claim 10, further comprising N number of bend sections in said beam line operable to bend said particle beam from said degrader into said N number of treatment rooms.

12. The treatment system described in claim 11 wherein said N number of bend sections are operable to perform energy analyzing functionality by modifying an energy width of said particle beam for a fixed beam line room.

13. The treatment system described in claim 12 further comprising a plurality of gantry beam lines operable to provide energy selection functionally for said N number of treatment rooms without using a separate achromatic beam line.

14. A treatment system comprising:
   an accelerator operable to extract a particle beam;
   a first beam line comprising quadrupole and steerer magnets operable to align and focus said particle beam from said accelerator to deliver said particle beam to a first treatment room and a second beam line;
   said second beam line to transports said particle beam to N number of treatment rooms;

a first bend section coupled to said second beam line and operable to direct said particle beam to a first treatment room;

a degrader disposed between said first bend section and said first treatment room, wherein said particle beam is focused on said degrader to modulate an energy of said particle beam; and a first gantry disposed in said first treatment room and operable to receive said particle beam downstream from said degrader, wherein said first gantry provides energy selection functionality for said first treatment room.

15. The treatment system described in claim 14, further comprising N number of bend sections in said beam line operable to bend said particle beam from said degrader into said N number of treatment rooms.

16. The treatment system described in claim 15, wherein said N number of bend sections are operable to perform energy analyzing functionality by modifying an energy width of said particle beam for a fixed beam line room without using a separate achromatic beam line.

17. The treatment system described in claim 16, further comprising a plurality of gantry beam lines operable to provide energy selection functionally for said N number of treatment rooms.

* * * * *